US012220181B2

(12) United States Patent
Payyavula et al.

(10) Patent No.: US 12,220,181 B2
(45) Date of Patent: Feb. 11, 2025

(54) CAMERA CONTROL SYSTEMS AND METHODS FOR A COMPUTER-ASSISTED SURGICAL SYSTEM

(71) Applicant: Intuitive Surgical Operations, Inc., Sunnyvale, CA (US)

(72) Inventors: Govinda Payyavula, Sunnyvale, CA (US); Anthony M. Jarc, Johns Creek, GA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 559 days.

(21) Appl. No.: 17/426,038

(22) PCT Filed: Jan. 28, 2020

(86) PCT No.: PCT/US2020/015396
§ 371 (c)(1),
(2) Date: Jul. 27, 2021

(87) PCT Pub. No.: WO2020/159978
PCT Pub. Date: Aug. 6, 2020

(65) Prior Publication Data
US 2022/0096163 A1    Mar. 31, 2022

Related U.S. Application Data

(60) Provisional application No. 62/799,729, filed on Jan. 31, 2019.

(51) Int. Cl.
*A61B 34/20*    (2016.01)
*A61B 34/00*    (2016.01)
(Continued)

(52) U.S. Cl.
CPC .............. *A61B 34/20* (2016.02); *A61B 34/10* (2016.02); *A61B 34/25* (2016.02); *A61B 34/70* (2016.02);
(Continued)

(58) Field of Classification Search
CPC ......... A61B 34/20; A61B 34/10; A61B 34/25; A61B 34/70; A61B 90/39; A61B 2034/2057; G16H 40/67; G16H 40/20
(Continued)

(56) References Cited

U.S. PATENT DOCUMENTS 9,788,907 B1* 10/2017 Alvi ..................... G11B 27/34
2005/0033580 A1* 2/2005 Wang ................. A61B 1/00042
704/E15.045
(Continued)

FOREIGN PATENT DOCUMENTS

JP    2012223363 A    11/2012
WO    WO-0069354 A1    11/2000
(Continued)

OTHER PUBLICATIONS

International Preliminary Report on Patentability for Application No. PCT/US2020/015396, mailed on Aug. 12, 2021, 13 pages.
(Continued)

*Primary Examiner* — Michael J Lau

(57) ABSTRACT

A camera control system may access surgical session data for a surgical session, the surgical session including performance of one or more operations by a computer-assisted surgical system. The camera control system may identify, based on the surgical session data, an event associated with the surgical session, and may determine, based on the surgical session data, a location associated with the event. In response to the determination of the location of the event, the camera control system may direct an automatic adjust-
(Continued)

ment of a view of a camera to capture a specific view of the location associated with the event.

20 Claims, 12 Drawing Sheets

(51) Int. Cl.
    *A61B 34/10*      (2016.01)
    *A61B 90/00*      (2016.01)
    *G16H 40/20*      (2018.01)
    *G16H 40/67*      (2018.01)

(52) U.S. Cl.
    CPC ............. *A61B 90/39* (2016.02); *G16H 40/20* (2018.01); *G16H 40/67* (2018.01); *A61B 2034/2057* (2016.02)

(58) Field of Classification Search
    USPC ............................................................. 606/1
    See application file for complete search history.

(56) References Cited

U.S. PATENT DOCUMENTS

2007/0268133 A1    11/2007    Sanchez et al.
2009/0245600 A1\*    10/2009    Hoffman ................ A61B 34/37
                                                        348/240.99
2014/0287393 A1\*    9/2014    Kumar .................... G09B 5/02
                                                         434/262
2017/0143442 A1\*    5/2017    Tesar ..................... A61B 90/37
2018/0055577 A1\*    3/2018    Barral ................... B25J 9/1633
2018/0092705 A1    4/2018    Ootsuki et al.
2018/0338806 A1\*    11/2018    Grubbs ................. A61B 34/30
2018/0368656 A1\*    12/2018    Austin .................. A61B 1/045

FOREIGN PATENT DOCUMENTS

WO    WO-2012100341 A1 \*    8/2012    ......... A61B 19/5212
WO    WO-2016149794 A1    9/2016
WO    WO-2017169135 A1    10/2017

OTHER PUBLICATIONS

International Search Report and Written Opinion for Application No. PCT/US2020/015396, mailed on Jun. 24, 2020, 17 pages.
Invitation to pay additional fee received from the International Search AuthorityforPCT/US2020/015396, mailed Apr. 17, 2020, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

| Event | Component |
|---|---|
| MA1_Collide_MA2 | MA1 |
| MA2_Collide_MA3 | MA2 |
| MA2_Collide_MA4 | MA2 |
| InstExchg_MA3 | MA3 |
| InstExchg_MA4 | MA4 |
| BedMotion | OpTable |
| MA1_Error | MA1 |
| MC_Collide | UCS |
| MA4_NoSignal | MA4 |

Fig. 9

CAMERA CONTROL SYSTEMS AND METHODS FOR A COMPUTER-ASSISTED SURGICAL SYSTEM

RELATED APPLICATIONS

The present application is a U.S. National Stage Application under 35 U.S.C. § 371 of International Application No. PCT/US2020/015396, filed on Jan. 28, 2020, which claims priority to U.S. Provisional Patent Application No. 62/799,729, filed on Jan. 31, 2019 the contents of which are hereby incorporated by reference in their entirety.

BACKGROUND INFORMATION

During a computer-assisted surgical procedure, such as a minimally invasive surgical procedure that uses a computer-assisted surgical system, a camera may capture, for example, imagery of a scene of the computer-assisted surgical system outside of the patient. The computer-assisted surgical system may display the captured imagery to medical personnel (e.g., to a surgeon and/or other members of a surgical team) to provide a visualization of the computer-assisted surgical system. The visualized imagery assists the medical personnel in performing the surgical procedure. However, a user typically must manually position and move the camera to capture the desired view, which takes time and interrupts the flow of the surgical procedure. As a result, the camera may not be fully utilized during the surgical procedure.

SUMMARY

An exemplary system may include a memory storing instructions and a processor communicatively coupled to the memory and configured to execute the instructions to access surgical session data for a surgical session, the surgical session including performance of one or more operations by a computer-assisted surgical system; identify, based on the surgical session data, an event associated with the surgical session; determine, based on the surgical session data, a location associated with the event; and direct, in response to the determination of the location of the event, an automatic adjustment of a view of a camera to capture a specific view of the location associated with the event.

An exemplary method may comprise accessing, by a camera control system, surgical session data for a surgical session, the surgical session including performance of one or more operations by a computer-assisted surgical system; identifying, by the camera control system based on the surgical session data, an event associated with the surgical session; determining, by the camera control system based on the surgical session data, a location associated with the event; and directing, by the camera control system in response to the determination of the location of the event, an automatic adjustment of a view of a camera to capture a specific view of the location associated with the event.

An exemplary system includes a memory storing instructions and a processor communicatively coupled to the memory and configured to execute the instructions to receive, from a user device communicatively paired with a computer-assisted surgical system during a surgical session, user input indicating a workflow segmentation of the surgical session; identify, based at least in part on the user input, an event associated with the surgical session; determine, based on surgical session data for the surgical session, a location associated with the identified event; and direct, in response to the determination of the location of the event, an automatic adjustment of a view of a camera to capture a specific view of the location associated with the event.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 9-10 illustrate exemplary event location tables according to principles described herein.

DETAILED DESCRIPTION

Figure 1:
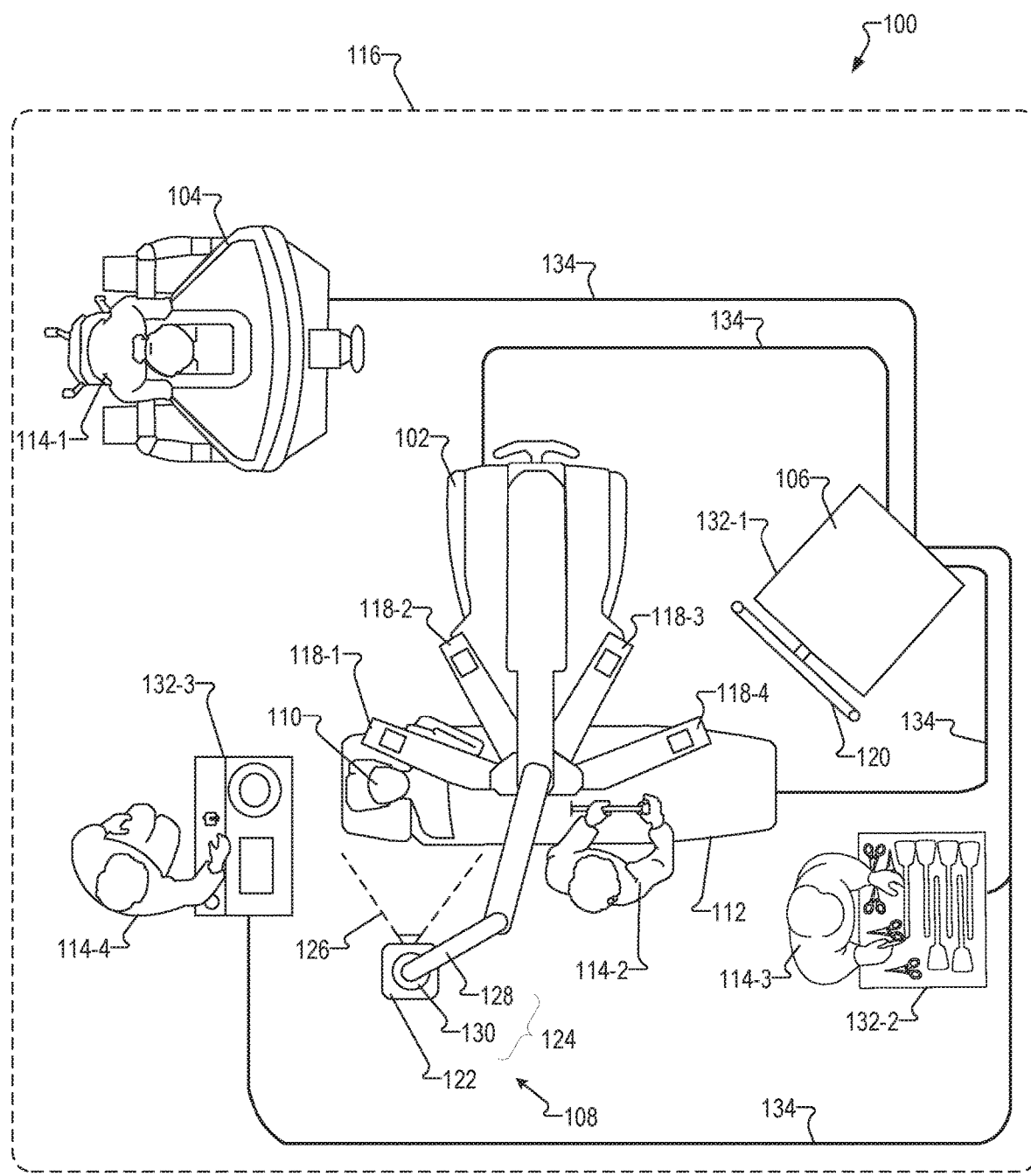
FIG. 1 illustrates an exemplary computer-assisted surgical system according to principles described herein.

Camera control systems and methods for a computer-assisted surgical system are described herein. As will be explained in more detail below, an exemplary camera control system may access surgical session data for a surgical session, the surgical session including performance of one or more operations by a computer-assisted surgical system. The camera control system may identify, based on the surgical session data, an event associated with the surgical session, and may determine, based on the surgical session data, a location associated with the event. In response to the determination of the location of the event, the camera control system may direct an automatic adjustment of a view of a camera to capture a specific view of the location associated with the event. In some examples, imagery captured by the camera may be displayed by a display device associated with the computer-assisted surgical system.

To illustrate, during a minimally-invasive surgical procedure performed at a surgical facility with a computer-assisted surgical system, a camera control system may detect that a first manipulator arm to which a surgical instrument is attached is colliding with a second manipulator arm, thus preventing movement of a tip of a surgical instrument coupled to the first manipulator arm. As a result, the camera control system may determine that a location of the collision event is a location of the first manipulator arm and direct an automatic adjustment of a camera positioned within the surgical facility to capture a specific view of the first manipulator arm. Video from the camera may be displayed by a display device associated with a user control system used by a surgeon. Thus, the surgeon may quickly see why the tip of the surgical instrument is not moving and may quickly identify corrective actions, all without leaving his or her position at the user control system.

Various benefits may be provided by the camera control systems and methods described herein. For example, the systems and methods described herein may automatically direct an adjustment of a camera positioned within a surgical facility to capture imagery based on a detected context of a surgical session. The automatic adjustment of the camera may improve the efficiency of a surgical session by eliminating the interruption caused by manually adjusting a camera. Additionally, the systems and methods described herein may provide surgical team members with relevant contextual information in real-time during a surgical procedure, which may result in more effective and efficient collaboration and coordination among the surgical team members, and which may allow surgical team members to quickly and efficiently troubleshoot problems. Moreover, the systems and methods may predict events that may occur during the surgical session and direct the presentation of contextual visual content associated with such events, thus allowing surgical team members to prepare for and/or resolve such events before they occur.

Numerous technical computing benefits may also be realized by the systems and methods described herein. For example, the systems and methods described herein may be configured to access, transform, and process data from disparate computing systems in a manner that allows the systems and methods to provide timely (e.g., real-time) information to various users by way of various computing platforms. To this end, the systems and methods described herein may seamlessly integrate with one or more special purpose computing devices to process various types of data (e.g., by applying kinematics data, image data, sensor data, and/or surgical instrument data to one or more machine learning models) in order to identify events that occur, or that may occur, during a surgical session and/or identify contextual information associated with the events. In addition, the systems and methods described herein may utilize historical surgical session data generated during surgical sessions that precede a current surgical session to determine a context of the surgical session with reference to the other prior surgical sessions. In this manner, the systems and methods described herein may perform operations that are impossible to perform by a human alone. Moreover, the systems and methods described herein may improve the operation of a computer-assisted surgical system by improving efficiency, accuracy, and effectiveness of the computer-assisted surgical system.

Various embodiments will now be described in more detail with reference to the figures. The systems and methods described herein may provide one or more of the benefits mentioned above and/or various additional and/or alternative benefits that will be made apparent herein.

In some implementations, a camera control system may operate as part of or in conjunction with a computer-assisted surgical system. As such, an exemplary computer-assisted surgical system will now be described. The described exemplary computer-assisted surgical system is illustrative and not limiting. The camera control system may operate as part of or in conjunction with the computer-assisted surgical system described herein and/or with other suitable computer-assisted surgical systems.

FIG. 1 illustrates an exemplary computer-assisted surgical system 100 ("surgical system 100"). As shown, surgical system 100 may include a manipulating system 102, a user control system 104, an auxiliary system 106, and an auxiliary camera system 108 communicatively coupled one to another. In some examples, the camera control systems described herein may be implemented by one or more of these components.

Surgical system 100 may be utilized by a surgical team to perform a computer-assisted surgical procedure on a patient 110 positioned on an operating table 112. As shown, the surgical team may include a surgeon 114-1, a nurse 114-2, an assistant 114-3, and an anesthesiologist 114-4, all of whom may be collectively referred to as "surgical team members 114." Additional or alternative surgical team members may be present during a surgical session as may serve a particular implementation. Surgical system 100 and surgical team members 114 are located at a surgical facility 116. As used herein, a "surgical facility" may include any area where surgical system 100 and surgical team members 114 are located when they perform the computer-assisted surgical procedure. For example, a surgical facility may include an operating room, a training facility, a particular area within a room, and the like. In some examples, surgeon 114-1 may be positioned in a room or location separate from a room or location where manipulating system 102, auxiliary system 106, and/or other surgical team members 114 are located during the surgical procedure. In these examples, the surgical facility may include either or both locations.

While FIG. 1 illustrates an ongoing minimally invasive surgical procedure at surgical facility 116, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any procedure that is not performed on a live patient, such as a calibration procedure, a training procedure, and an experimental or research procedure.

As shown in FIG. 1, manipulating system 102 may include a plurality of manipulator arms 118 (e.g., manipulator arms 118-1 through 118-4) to which a plurality of surgical instruments (not shown) may be coupled. Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure (e.g., by being at least partially inserted into patient 110 and manipulated to perform a computer-assisted surgical procedure on patient 110). While manipulating system 102 is depicted and described herein as including four manipulator arms 118, it will be recognized that manipulating system 102 may include only a single manipulator arm 118 or any other number of manipulator arms as may serve a particular implementation.

Surgical instruments coupled to manipulator arms 118 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 114-1 of manipulator arms 118 and surgical instruments coupled to manipulator arms 118. For example, surgeon 114-1 may interact with user control system 104 to remotely move or manipulate manipulator arms 118 and surgical instruments. To this end, user control system 104 may provide surgeon 114-1 with imagery (e.g., high-definition stereoscopic imagery) of a surgical area associated with patient 110 as captured by an imaging device (e.g., an endoscope). In certain examples, user control system 104 may include a stereo viewer having two displays where stereoscopic images of a surgical area associated with patient 110 and generated by a stereoscopic imaging system may be viewed by surgeon 114-1. Surgeon 114-1 may utilize the imagery to perform one or more procedures with one or more surgical instruments coupled to manipulator arms 118.

To facilitate control of surgical instruments, user control system 104 may include a set of master controls (not shown). These master controls may be manipulated by surgeon 114-1 to control movement of surgical instruments (e.g., by utilizing robotic and/or teleoperation technology). The master controls may be configured to detect a wide variety of hand, wrist, and finger movements by surgeon 114-1. In this manner, surgeon 114-1 may intuitively perform a surgical procedure using one or more surgical instruments.

User control system 104 may further be configured to facilitate control by surgeon 114-1 of other components of surgical system 100. For example, surgeon 114-1 may interact with user control system 104 to change a configuration or operating mode of surgical system 100, to change a display mode of surgical system 100, to generate additional control signals used to control surgical instruments attached to manipulator arms 118, to facilitate switching control from one surgical instrument to another, or to perform any other suitable operation. To this end, user control system 104 may also include one or more input devices (e.g., foot pedals, buttons, switches, etc.) configured to receive input from surgeon 114-1.

Auxiliary system 106 may include one or more computing devices configured to perform primary processing operations of surgical system 100. The one or more computing devices included in auxiliary system 106 may control and/or coordinate operations performed by various other components (e.g., manipulating system 102, surgical instruments attached to manipulator arms 118, and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102 and process image data representative of imagery captured by an imaging device attached to one of manipulator arms 118.

In some examples, auxiliary system 106 may be configured to present visual content to surgical team members 114 who may not have access to the images provided to surgeon 114-1 at user control system 104. To this end, auxiliary system 106 may include a display monitor 120 configured to display one or more user interfaces, such as images (e.g., 2D images) of the surgical area, information associated with patient 110 and/or the surgical procedure, and/or any other visual content as may serve a particular implementation. For example, display monitor 120 may display images of the surgical area together with additional content (e.g., graphical content, contextual information, etc.) concurrently displayed with the images. In some embodiments, display monitor 120 is implemented by a touchscreen display with which surgical team members 114 may interact (e.g., by way of touch gestures) to provide user input to surgical system 100.

Auxiliary camera system 108 may be configured to capture and provide, on one or more display devices of surgical system 100, visual content based on a detected context of the surgical procedure. As shown in FIG. 1, auxiliary camera system 108 may include an auxiliary camera 122 ("camera 122") coupled to a camera manipulating system 124. Camera 122 may be implemented by any suitable camera. In some examples, camera 122 may be implemented by a plurality of imaging devices configured to provide stereoscopic imagery. While auxiliary camera system 108 is depicted and described herein as including one camera 122, it will be recognized that auxiliary camera system 108 may include multiple cameras 122 as may serve a particular implementation. For instance, if user control system 104 and surgeon 114-1 are located remotely from other components of surgical system 100, an additional camera may be positioned to capture and provide imagery of user control system 104 and surgeon 114-1.

Imagery (e.g., one or more still images or video images) captured by camera 122 may be transmitted to and/or displayed by any suitable display device associated with surgical system 100. For example, imagery captured by camera 122 may be transmitted to and displayed by display monitor 120, a stereo viewer of user control system 104, a mobile device communicatively paired with surgical system 100 during the surgical session (e.g., a mobile device used by assistant 114-3), and/or a display device associated with a remote computing device. In some examples in which surgical system 100 includes dual user control systems 104, such as for training a surgeon to use surgical system 100, imagery captured by camera 122 may be displayed by a display device associated with a second user control system 104 for viewing by another user (e.g., a remote proctor monitoring the surgical session and/or training the surgeon). Additionally or alternatively, image data representative of the imagery captured by camera 122 may be streamed and/or recorded by a remote computing device, thereby enabling playback of the imagery at a later time (e.g., after the surgical session).

Camera manipulating system 124 may be configured to automatically adjust a position and/or orientation of camera 122 to capture a specific view 126 within surgical facility 116. As used herein, a "position" of camera 122 within surgical facility 116 may refer to a particular location of camera 122 within a three-dimensional ("3D") space, and an "orientation" of camera 122 may refer to an imaging direction (e.g., view 126) of camera 122, which may be any direction within the 3D space.

Camera manipulating system 124 may be implemented by any suitable mechanism(s) configured to adjust a position and/or orientation of camera 122. For example, as shown in FIG. 1, camera manipulating system 124 may include a camera manipulator arm 128 to which camera 122 is coupled by way of camera pivot 130. Camera manipulator arm 128 may be configured to adjust a position and/or an orientation of camera 122 by movement of camera manipulator arm 128. Camera pivot 130 may be configured to adjust an orientation of camera 122. For example, camera pivot 130 may rotate camera 122 within a horizontal plane, such as by panning from left to right (as viewed in the imaging direction of camera 122). Additionally or alternatively, camera pivot 130 may tilt camera 122 up or down within a vertical plane, such as by adjusting the imaging direction of camera 122 up or down (i.e., at an angle relative to a horizontal plane). Camera manipulating system 124 may include additional or alternative components as may serve a particular implementation. For example, camera manipulating system 124 may include various gears, motors, arms, pivots, joints, bearings, and any other electrical and/or mechanical components that may facilitate adjustment of the position and/or orientation of camera 122.

Camera manipulating system 124 of auxiliary camera system 108 may be configured to adjust a position and/or orientation of camera 122 in any suitable manner. In some examples, the position and/or orientation of camera manipulating system 124 may be adjusted manually, such as by a user pushing or moving camera 122 to a desired position or operating one or more electronic controls of camera manipulating system 124. Additionally or alternatively, the position and/or orientation of camera 122 may be adjusted automatically (e.g., without user input) based on a context of the surgical session (e.g., based on an event associated with the surgical session), as will be explained below in more detail.

As shown in FIG. 1, auxiliary camera system 108 (e.g., camera manipulating system 124) is coupled to manipulating system 102. In alternative examples, auxiliary camera system 108 may be coupled to any other component of surgical system 100 as may suit a particular implementation, such as user control system 104, auxiliary system 106, or a cart 132 (e.g., instrument cart 132-2. In additional examples, auxiliary camera system 108 may be separate from manipulating system 102, user control system 104, and auxiliary system 106. For example, camera manipulating system 124 may be mounted to a wall of an operating room. Alternatively, auxiliary camera system 108 may be a standalone system within surgical facility 116, as shown in FIG. 2.

Figure 2:
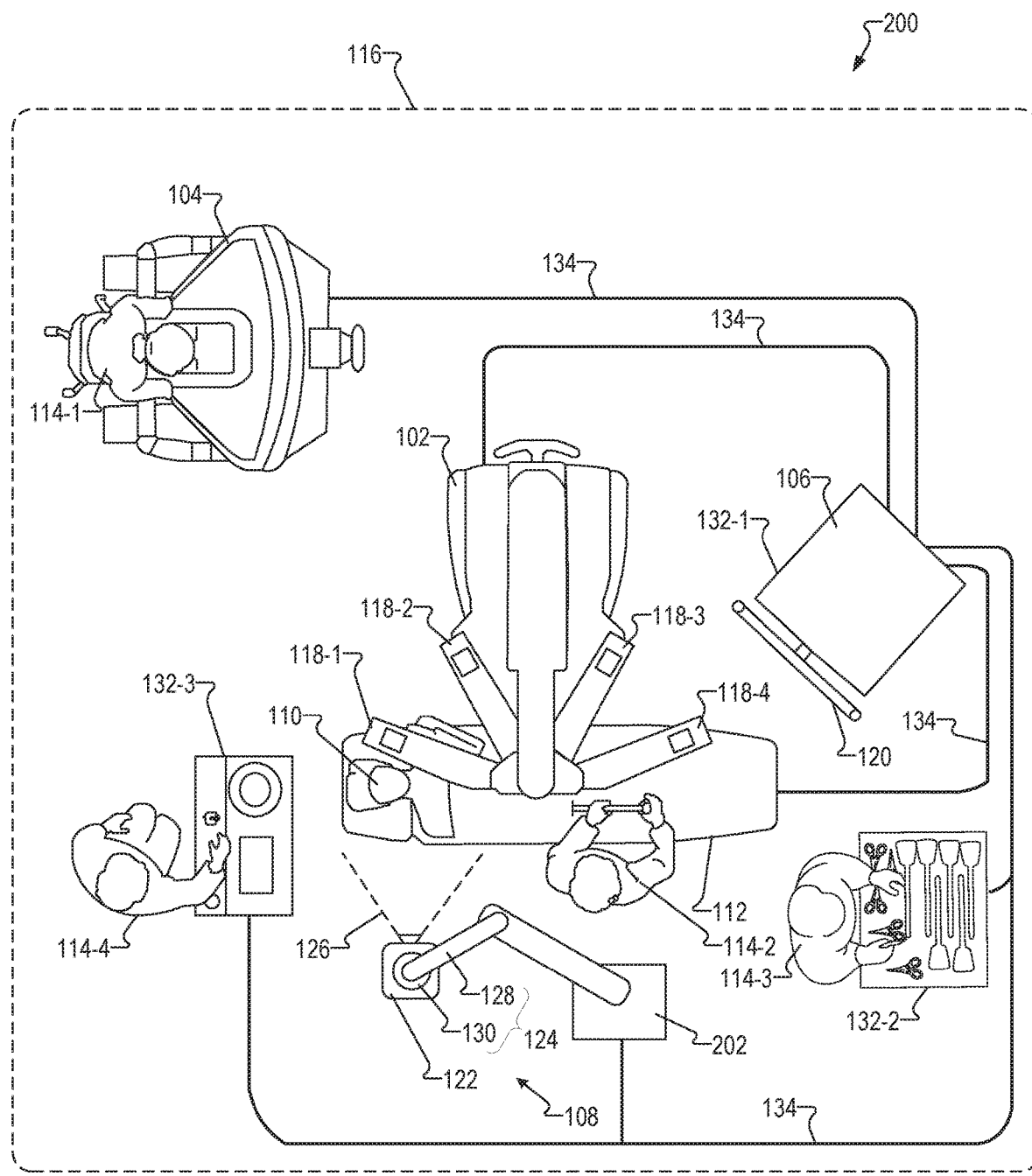
FIG. 2 illustrates another exemplary computer-assisted surgical system according to principles described herein.

FIG. 2 is the same as FIG. 1 except that auxiliary camera system 108 includes a movable camera cart 202. Camera manipulating system 124 is supported on camera cart 202, thereby allowing a surgical team member 114 to easily position camera 122 at a desired location within surgical facility 116 by moving camera cart 202. Additionally, a surgical team member 114 may move camera cart 202 as necessary during the surgical procedure.

Referring again to FIG. 1, surgical system 100 may also include one or more movable carts 132 for holding certain components of surgical system 100 and/or supplies to be used during the surgical procedure. For example, one or more computing devices included in auxiliary system 106 may be housed within auxiliary cart 132-1. Additionally, surgical instruments that are not coupled to a manipulator arm 118 may be stowed on an instrument cart 132-2 for easy access (e.g., by assistant 114-3) when coupling surgical instruments to a manipulator arm 118 and/or swapping surgical instruments during the surgical procedure. Supply cart 132-3 may be used, for example, by anesthesiologist 114-4 to store medications and/or other agents (e.g., fluorescence imaging agents) that may be administered to patient 110 during the surgical procedure.

Various components of surgical system 100 may include one or more displacement transducers, orientational sensors, and/or positional sensors used to generate raw (i.e., uncorrected) kinematics information (hereinafter "surgical system sensors"). For example, user control system 104, auxiliary system 106, auxiliary camera system 108, operating table 112, manipulator arms 118, surgical instruments attached to manipulator arms 118, and carts 132 may include one or more surgical system sensors. Surgical system 100 (e.g., auxiliary system 106) may be configured to use the kinematics information to track (e.g., determine positions of) and/or control the various components of surgical system 100.

Components of surgical system 100 may be communicatively coupled one to another in any suitable manner. For example, as shown in FIG. 1, manipulating system 102, user control system 104, auxiliary system 106, auxiliary camera system 108, and carts 118 may be communicatively coupled by way of control lines 134, which may represent any wired or wireless communication link as may serve a particular implementation. To this end, manipulating system 102, user control system 104, auxiliary system 106, auxiliary camera system 108, and carts 132 may each include one or more wired or wireless communication interfaces, such as one or more local area network interfaces, Wi-Fi network interfaces, cellular interfaces, etc.

Figure 3:
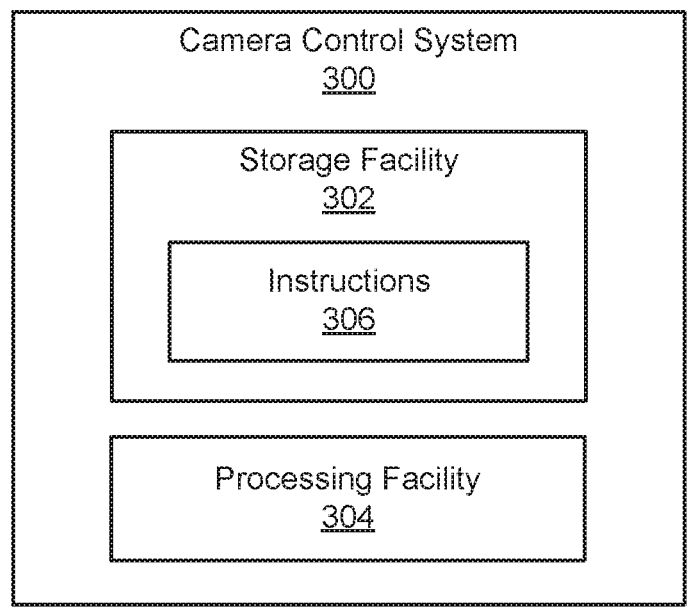
FIG. 3 illustrates an exemplary camera control system according to principles described herein.

As mentioned, the position and/or orientation of camera 122 may be adjusted automatically based on a context of the surgical session to capture a specific view (e.g., view 126) within surgical facility 116. FIG. 3 illustrates an exemplary camera control system 300 configured to automatically control certain operations of a camera system associated with a computer-assisted surgical system (e.g., auxiliary camera system 108, an endoscope coupled to a manipulator arm 118, a plurality of cameras associated with the computer-assisted surgical system, etc.) to provide contextual visual content associated with an event associated with a computer-assisted surgical session. As shown, camera control system 300 may include, without limitation, a storage facility 302 and a processing facility 304 selectively and communicatively coupled to one another. Facilities 302 and 304 may each include or be implemented by hardware and/or software components (e.g., processors, memories, communication interfaces, instructions stored in memory for execution by the processors, etc.). In some examples, facilities 302 and 304 may be distributed between multiple devices and/or multiple locations as may serve a particular implementation.

Storage facility 302 may maintain (e.g., store) executable data used by processing facility 304 to perform any of the operations described herein. For example, storage facility 302 may store instructions 306 that may be executed by processing facility 304 to perform any of the operations described herein. Instructions 306 may be implemented by any suitable application, software, code, and/or other executable data instance.

Storage facility 302 may also maintain any data received, generated, managed, used, and/or transmitted by processing facility 304. For example, as will be described below in more detail, storage facility 302 may maintain surgical session data, user profile data, user input data, and the like.

Processing facility 304 may be configured to perform (e.g., execute instructions 306 stored in storage facility 302 to perform) various processing operations associated with automatically adjusting a view of a camera to capture a specific view of a location associated with an event associated with a surgical session. For example, processing facility 304 may access surgical session data for a surgical session. The surgical session may include performance of one or more operations by a computer-assisted surgical system (e.g., surgical system 100). Processing facility 304 may identify, based on the surgical session data, an event associated with the surgical session, such as an event that has occurred or an event that is likely to occur. Based on the surgical session data, processing facility 304 may determine a location associated with the event and may direct, in response to the determination of the location of the event, an automatic adjustment of a view of a camera (e.g., camera 122) to capture a specific view of the location associated with the event. These and other operations that may be performed by processing facility 304 are described herein in more detail.

In some examples, camera control system 300 is implemented entirely by the computer-assisted surgical system itself. For example, camera control system 300 may be implemented by one or more computing devices included in surgical system 100 (e.g., in one or more computing devices included within manipulating system 102, user control system 104, auxiliary system 106, and/or auxiliary camera system 108).

Figure 4:
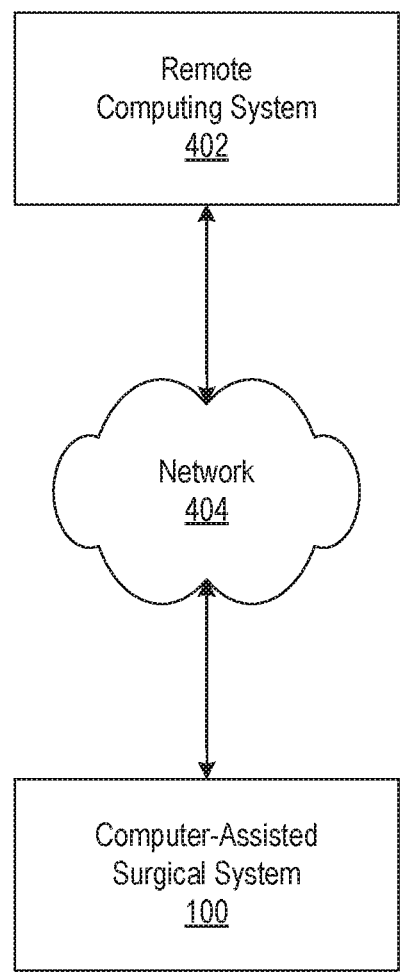
FIG. 4 illustrates an exemplary implementation of the camera control system illustrated in FIG. 3 according to principles described herein.

FIG. 4 illustrates another exemplary implementation 400 of camera control system 300. In implementation 400, a remote computing system 402 may be communicatively coupled to surgical system 100 by way of a network 404. Remote computing system 402 may include one or more computing devices (e.g., servers) configured to perform any of the operations described herein. In some examples, camera control system 300 may be entirely implemented by remote computing system 402. Alternatively, camera control system 300 may be implemented by both remote computing system 402 and surgical system 100.

Network 404 may be a local area network, a wireless network (e.g., Wi-Fi), a wide area network, the Internet, a cellular data network, and/or any other suitable network. Data may flow between components connected to network 404 using any communication technologies, devices, media, and protocols as may serve a particular implementation.

Figure 5:
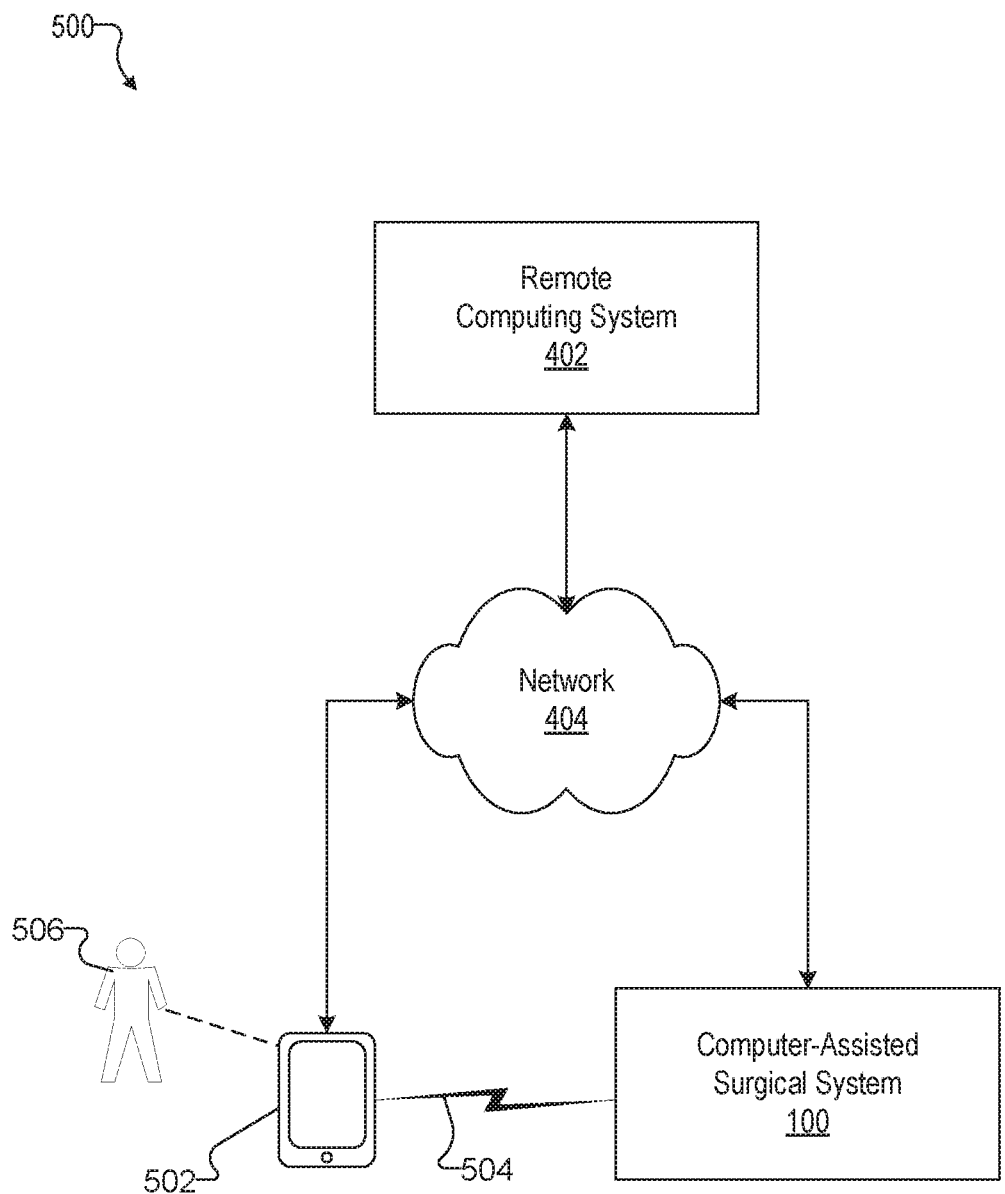
FIG. 5 illustrates another exemplary implementation of the camera control system illustrated in FIG. 3 according to principles described herein.

FIG. 5 illustrates another exemplary implementation 500 of camera control system 300. FIG. 5 is similar to FIG. 4 except that a user device 502 may be communicatively paired with surgical system 100 and connected to network 404. As shown, user device 502 may communicate with remote computing system 402 and/or surgical system 100 by way of network 404. Additionally or alternatively, user device 502 may communicate with surgical system 100 by way of a direct connection 504 (e.g., a direct wired connection and/or a direct wireless connection, such as a Bluetooth connection, a near field communication connection, and the like). In some examples, camera control system 300 may be implemented by remote computing system 402, surgical system 100, and/or user device 502.

User device 502 may be any suitable computing device configured to receive and transmit user input and/or present visual content. For example, user device 502 may be, but is not limited to, a mobile device (e.g., a mobile phone, a handheld device, a tablet computing device, a laptop computer, a personal computer, etc.), a wearable device (e.g., a smartwatch device, an activity tracker, a head-mounted display device, a virtual or augmented reality device, etc.), and/or a display device (e.g., a television, a projector, a monitor, a touch screen display device, etc.).

As shown, a user 506 (e.g., a surgical team member 114) may use or otherwise have access to user device 502. In some examples, user 506 may have to be logged in to user device 502 or to an application executed by user device 502 in order to use and/or interact with user device 502. In some examples, the application executed by user device 502 may be used by user 506 to provide user input regarding workflow segmentation of the surgical session and to view imagery captured by a camera (e.g., camera 122). For instance, user 506 may provide input regarding a task completed by user 506 or another surgical team member (e.g., one or more operations performed by a surgical team member or the computer-assisted surgical system), a stage of a surgical procedure, a condition of a patient, a malfunction of a component of the surgical system, a change in personnel on the surgical team, and any other information as may suit a particular implementation. As will be explained below in more detail, such user input may be utilized by camera control system 300 to more accurately identify surgical session events that occur, or that may occur, during a surgical session.

Although FIG. 5 shows only one user device 502 communicatively paired with surgical system 100 and connected to network 404, any number of user devices 502 may be paired with surgical system 100 and/or connected to network 404. For example, each surgical team member 114 may utilize, during a surgical session, a user device 502 to provide input regarding a workflow of the surgical session, as well as to view imagery captured by a camera (e.g., camera 122).

Various operations that may be performed by camera control system 300 (e.g., by processing facility 304 of camera control system 300), and examples of these operations, will now be described. It will be recognized that the operations and examples described herein are merely illustrative of the many different types of operations that may be performed by camera control system 300.

Camera control system 300 may direct an automatic adjustment of a view of a camera (e.g., view 126 of camera 122) to capture a specific view of a location associated with a surgical session event. To this end, camera control system 300 may access surgical session data for a surgical session and, based on the surgical session data, identify an event associated with the surgical session. Various examples of these operations will now be provided.

In some examples, surgical session data accessed by camera control system 300 may be generated during the surgical session and may be based on one or more operations performed by a computer-assisted surgical system (e.g., surgical system 100) during the surgical session. The operations performed by the computer-assisted surgical system may include any mechanical, electrical, hardware, and/or software-based operations as may serve a particular implementation. The surgical session data may be generated by the computer-assisted surgical system (e.g., by one or more components within surgical system 100), by one or more components coupled to the computer-assisted surgical system during the surgical session (e.g., one or more surgical instruments coupled to a manipulator arm 118), by a user device (e.g., user device 502) communicatively paired with the computer-assisted surgical system during the surgical session, and/or by any other device associated with the computer-assisted surgical system as may serve a particular implementation. In scenarios in which camera control system 300 is implemented entirely by remote computing system 402, surgical session data may additionally or alternatively be generated by remote computing system 402 while, for example, remote computing system 402 tracks operations performed by surgical system 100.

Surgical session data generated during a surgical session may include various types of data. For example, surgical session data generated during a surgical session may include kinematic data, image data, sensor data, surgical instrument data, and/or any other type of data as may serve a particular implementation.

Kinematic data may be representative of a position, a pose, and/or an orientation of a component within the computer-assisted surgical system and/or a component coupled to the computer-assisted surgical system. For example, kinematic data may be representative of a position, a pose, and/or an orientation of a manipulator arm 118 and/or a surgical instrument coupled to a manipulator arm 118. As another example, kinematic data may be representative of a position of manipulating system 102, user control system 104, auxiliary camera system 108, operating table 112, and/or carts 132.

Image data may be representative of one or more images captured by an imaging device coupled to the computer-assisted surgical system. For example, image data may be representative of one or more images captured by an imaging device (e.g., a stereoscopic endoscope) coupled to a manipulator arm 118. The one or more images may constitute one or more still images and/or video captured by the imaging device. In some examples, camera control system 300 may access image data by receiving (e.g., by way of a network) images output by the imaging device. In additional or alternative examples, image data may include image data generated by an imaging device that is external to a patient, such as camera 122.

Sensor data may include any data generated by surgical system sensors included in or associated with a computer-assisted surgical system. Sensor data may be representative of any sensed parameter as may serve a particular implementation. For example, sensor data may be indicative of whether operating table 112 is moving, or whether surgeon 114-1 is actively interacting with user control system 104.

Surgical instrument data may include any data generated by a surgical instrument, and may be representative of an identification ("ID") of the surgical instrument, an operational state of the surgical instrument (e.g., open, closed, electrically charged, idle, etc.), a fault code of the surgical instrument, etc.

In some examples, camera control system 300 may additionally or alternatively access surgical session data generated by the computer-assisted surgical system during one or more other surgical sessions that, for example, precede the current surgical session. For example, camera control system 300 may generate surgical session data during a first surgical session in which the computer-assisted surgical system is used to perform a first surgical procedure with respect to a first patient. Camera control system 300 may also generate additional surgical session data during a second surgical session in which the computer-assisted surgical system is used to perform a second surgical procedure with respect to the patient or another patient. During the second surgical session, camera control system 300 may access both the surgical session data and the additional surgical session data. Surgical session data that is generated prior to a current surgical session may be referred to herein as "historical surgical session data." As will be described below, historical surgical session data may allow camera control system 300 to more effectively identify and/or predict an event that may occur during the second surgical session.

Camera control system 300 may additionally or alternatively access surgical session data based on operations performed by one or more computer-assisted surgical systems other than the computer-assisted surgical system being used during a particular surgical session. For example, camera control system 300 may access surgical session data generated during a plurality of distinct computer-assisted surgical sessions located within a particular medical center, a network of hospitals, and/or any other grouping. This type of surgical session data may be referred to herein as "global surgical session data" and, as will be described below, may allow camera control system 300 to more effectively identify and/or predict an event that may occur during a particular surgical session in which a particular computer-assisted surgical system included in the grouping is used to perform a surgical procedure.

In some examples, camera control system 300 may provide a user interface configured to allow a user to define a particular grouping of computer-assisted surgical sessions and/or computer-assisted surgical systems from which surgical session data may be accessed by camera control system 300.

Camera control system 300 may identify an event associated with a computer-assisted surgical session (a "surgical session event") based on surgical session data for the surgical session, historical surgical session data, and/or global surgical session data. A surgical session event may include any distinct operation or action that occurs, or that may occur, with respect to the computer-assisted surgical system during the surgical session. A surgical session event may occur during a preoperative phase, an operative phase, and/or a postoperative phase of a surgical procedure.

For example, a surgical session event may include any operation or action associated with various preoperative phase operations. Exemplary preoperative phase operations may include, but are not limited to, patient intake (e.g., admitting the patient to a medical facility, receiving patient documentation, etc.), preparing an operating room, sterilizing surgical instruments, testing the computer-assisted surgical system and equipment, draping the computer-assisted surgical system (i.e., covering one or more components of computer-assisted surgical system, such as manipulator arms 118, with a sterile or protective covering), preparing the patient for the surgical procedure (e.g., checking patient vital signs, providing intravenous fluids, administering anesthesia to the patient, bringing the patient into the operating room), and targeting the computer-assisted surgical system with respect to the patient (e.g., positioning manipulating system 102 at the patient bedside and positioning or configuring one or more manipulator arms 118).

A surgical session event may additionally or alternatively include any operation or action associated with various operative phase operations. Exemplary operative phase operations may include, but are not limited to, opening a surgical area associated with a patient (e.g., by making an incision on external patient tissue), inserting a surgical instrument into the patient, performing surgical operations on patient tissue (e.g., by cutting tissue, repairing tissue, suturing tissue, cauterizing tissue, etc.), and closing the surgical area associated with the patient (e.g., removing surgical instruments from the patient, suturing closed the incision point, dressing any wounds, etc.).

A surgical session event may additionally or alternatively include any operation or action associated with various postoperative phase operations. Exemplary postoperative phase operations may include, but are not limited to, removing the computer-assisted surgical system from the patient (e.g., removing manipulating system 102 from the patient bedside), patient care and recovery operations (e.g., removing the patient from the operating room, monitoring the patient as the patient recovers from the surgical procedure, etc.), cleaning the operating room, cleaning the computer-assisted surgical system and/or surgical instruments, receiving reporting documentation by surgical team members, and patient discharge operations.

Figure 6:
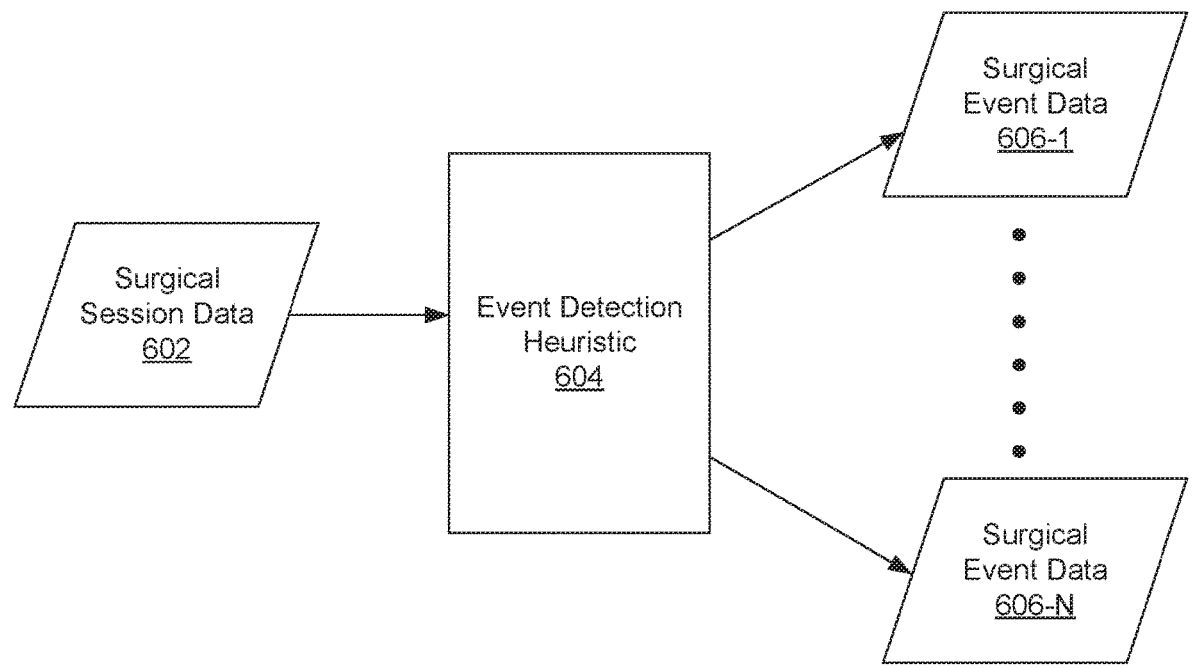
FIGS. 6-8 illustrate exemplary manners in which an event may be identified based on surgical session data and/or additional data according to principles described herein.

Camera control system 300 may identify a surgical session event based on surgical session data in any suitable manner. FIG. 6 shows an exemplary manner in which camera control system 300 may identify a surgical session event based on surgical session data. As shown, camera control system 300 may apply surgical session data 602 as an input to an event detection heuristic 604. Event detection heuristic 604 may analyze the surgical session data 602 and output various instances of event data 606 (e.g., event data 606-1 through event data 606-N). Each instance of event data 606 may represent a particular surgical session event identified by event detection heuristic 604.

Event detection heuristic 604 may include any suitable heuristic, process, and/or operation that may be performed or executed by camera control system 300 and that may be configured to identify events based on surgical session data 602. To illustrate, event detection heuristic 604 may detect an indicator and/or pattern in surgical session data that is indicative of an occurrence of a particular surgical session event.

For example, kinematic data generated during a particular portion of a surgical session may indicate movement of a surgical instrument in a suturing pattern. Additionally, surgical instrument data may indicate that the surgical instrument used during the same portion of the surgical session is a needle driver. Based on this kinematic data and surgical instrument data, camera control system 300 may determine that a suturing event is occurring or has occurred.

As another example, image data representative of images generated by an endoscope may indicate that a particular surgical instrument has remained out of a view of the endoscope for a predetermined period of time. Such image data may be indicative of an idle state event (e.g., that the surgical instrument is in an idle state).

In some examples, surgical session data 602 may include historical surgical session data, as described above. In these examples, one of the event data instances 606 output by event detection heuristic 604 may be representative of a surgical session event that camera control system 300 predicts will occur based on the historical surgical session data. For example, the historical surgical session data may include surgical session data generated during multiple surgical sessions in which the same type of surgical procedure is performed with the computer-assisted surgical system. Based on this historical surgical session data, event detection heuristic 604 may predict that a certain second event will occur following the occurrence of a certain first event.

In some examples, surgical session data 602 may include global surgical session data, as described above. In these examples, one of the surgical event data instances 606 output by event detection heuristic 604 may be representative of a surgical session event that is determined to occur based on the global surgical session data. For example, the global surgical session data may indicate that a particular kinematic data value for a particular surgical tool indicates that the surgical tool is located within a predetermined distance from patient tissue. When the actual kinematic data for the surgical tool being used during the surgical session is equal to or less than this value, event detection heuristic 604 may detect a surgical session event that indicates that the surgical tool is actually located within the predetermined distance from patient tissue.

Figure 7:
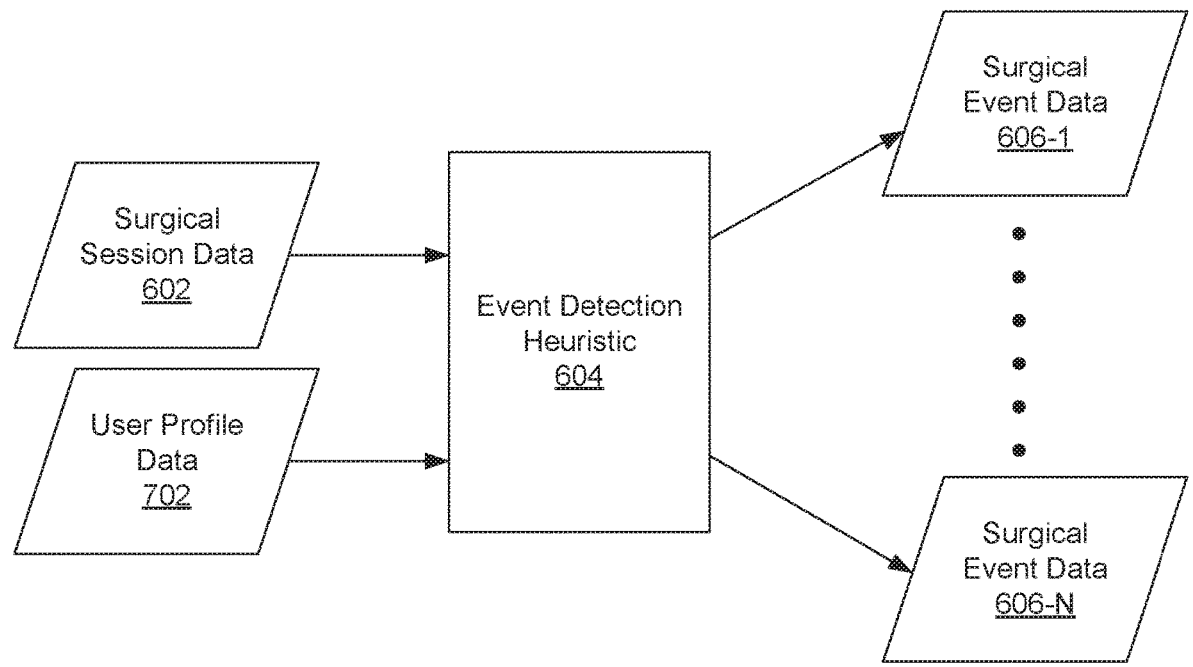

Event detection heuristic 604 may receive additional or alternative types of input as may serve a particular implementation. For example, FIG. 7 is similar to FIG. 6, but shows that event detection heuristic 604 may accept user profile data 702 (e.g., data representative of a user profile of one or more surgical team members involved with a surgical session) as an additional input. In this configuration, event detection heuristic 604 may detect surgical session events based on both surgical session data 602 and user profile data 702.

To illustrate, user profile data 702 may include data representative of a user profile of a surgeon (e.g., surgeon 114-1) involved with a surgical session. The user profile for the surgeon, combined with the surgical session data, may indicate that the surgeon performs various operations in a certain order unique to the surgeon. Accordingly, event detection heuristic 604 may detect that a particular surgical session event is going to occur in accordance with the certain order.

Figure 8:
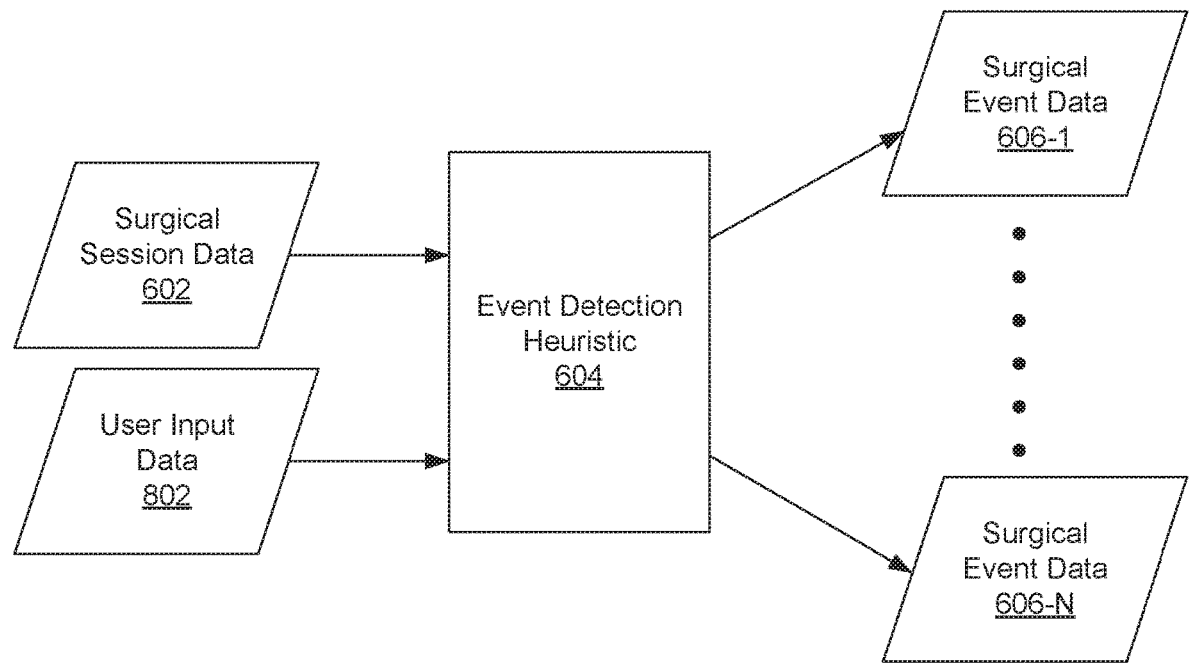

FIG. 8 illustrates another example of receiving additional or alternative types of input. FIG. 8 is similar to FIG. 6, but shows that event detection heuristic 604 may accept user input data 802 as an additional input. User input data 802 may be representative of information input by a user by way of a computing device included in the computer-assisted surgical system (e.g., by way of user control system 104 or auxiliary system 106) or communicatively paired with the computer-assisted surgical system (e.g., user device 502). In this configuration, event detection heuristic 604 may detect surgical session events based on both surgical session data 602 and user input data 802. User input data 802 may include, for example, information input by way of an application executed by a user device associated with a surgical team member.

To illustrate, user 506 (e.g., anesthesiologist 114-4) may input, via an application currently being executed by user device 502, information indicating that patient 110 is fully sedated. This information, combined with the surgical session data, may indicate that a preoperative phase of the surgical session has ended. Accordingly, event detection heuristic 604 may detect that a particular surgical session event is likely to occur, such as opening of an incision site on patient 110. Thus, camera control system 300 may direct an automatic adjustment of camera 122 to capture a specific view of a location associated with the next event, such as instrument cart 132-2.

In some examples, event detection heuristic 604 may implement a machine learning model. The machine learning model may use historical surgical session data, global surgical session data, user profile data, user input data, or any combination or sub-combination thereof, to identify one or more unique patterns of surgical system operations and associate surgical session events with the detected patterns of surgical system operations. As camera control system 300 collects more data, event data 606 output by event detection heuristic 604 may be updated or corrected as necessary.

When camera control system 300 identifies a surgical session event, camera control system 300 may determine a location, within the surgical facility, associated with the identified surgical session event (the "event location"). Camera control system 300 may then direct an automatic adjustment by a camera system associated with the computer-assisted surgical system (e.g., auxiliary camera system 108) to automatically adjust a view of a camera (e.g., view 126 of camera 122) to capture a specific view of the event location.

Camera control system 300 may determine the event location in any suitable way. In some examples, camera control system 300 may determine the event location by determining a location of the component associated with the identified surgical session event (the "event component"). To this end, in certain implementations camera control system 300 may access an event location table to identify a component associated with the identified surgical session event. To illustrate, FIG. 9 shows an exemplary event location table 900 that may be maintained or otherwise accessed by camera control system 300. As shown in column 902, table 900 may include a plurality of entries representative of various surgical session events that may occur during a surgical session (e.g., manipulator arm collision events, instrument exchange events, a bed motion event, a manipulator arm error event, a master controller collision event, and a manipulator arm no signal event). As shown in column 904, table 900 may also list a component associated with each surgical session event (e.g., a particular manipulator arm, an operation table, a user control system, and an auxiliary cart).

Once the event component has been identified, camera control system 300 may determine the location of the event component (the "component location") in any suitable way. In some examples, camera control system 300 may determine the component location based on surgical session data generated during the surgical session. For example, camera control system 300 may be configured to determine the component location based on kinematic data generated during the surgical session for the event component. Additionally or alternatively, the event location table may list component location data representative of a current location of each component listed in the event location table. The component location data may be populated when the surgical session begins and updated throughout the surgical session based on surgical session data (e.g., kinematic data) generated during the surgical session.

Additionally or alternatively to accessing kinematic data, camera control system 300 may determine the component location based on component tracking. In some examples, camera control system 300 may utilize marker-based computer vision tracking. To this end, unique markers (e.g., bar codes, colors, patterns, shapes, etc.) may be integrated on or otherwise attached to various components of the computer-assisted surgical system (e.g., manipulator arms 118, surgical instruments, carts 132, etc.), and the event location table may list marker data representative of a unique marker associated with each component. Camera control system 300 may access the event location table to identify a particular marker data instance associated with the event component. Based on the identified marker data instance, camera control system 300 may then determine the component location by detecting, in imagery captured by the camera system, the marker associated with the event component.

In additional or alternative examples, camera control system 300 may utilize signal-based tracking to determine the component location. To this end, emitters may be integrated on or otherwise attached to various components of the computer-assisted surgical system (e.g., manipulator arms 118, surgical instruments, carts 132, etc.), and the camera system may include a sensor configured to detect the signals emitted from the components. The emitters may be configured to emit any suitable signal, such as an infrared ("IR") signal. Each emitter may be configured emit a unique signal based on, for example, a unique wavelength, a unique flashing pattern, a unique frequency, etc. The event location table may list signal data representative of a unique signal associated with each component. Camera control system 300 may access the event location table to identify a particular signal data instance associated with the event component. Camera control system 300 may then direct the event component to emit its particular signal. Alternatively, the components may periodically emit their associated signals. Camera control system 300 may then identify the component location as the source of an emitted signal that matches the identified signal data instance associated with the event component.

Once camera control system 300 has determined the event location, camera control system 300 may direct an automatic adjustment of a view of a camera to capture a specific view of the event location. In some examples, camera control system 300 may cause a camera manipulating system to which a camera is coupled to adjust a position and/or an orientation of the camera to capture the specific view of the event location. In alternative examples in which the camera system is implemented by a standalone computing device, camera control system 300 may transmit, to the camera system, data representative of the event location and a command to adjust the position and/or the orientation of the camera to capture the specific view of the event location.

In some examples in which camera control system determines the event location based on marker-based tracking or signal-based tracking, camera control system 300 may direct an adjustment of the camera toward the marker or the emitted signal associated with the event location.

In additional or alternative examples, the amount and direction of the adjustment of the position and/or orientation of the camera may be determined based on a spatial relationship between the camera and the event location. In some examples in which the camera system is physically coupled (e.g., mounted) directly on a component of the surgical system, a spatial relationship between the camera and the event location may be determined based on surgical session data (e.g., kinematic data, sensor data, etc.). Accordingly, adjustment of the view of the camera may be based on surgical session data. For example, camera control system 300 may determine, based on kinematic data and sensor data associated with the camera system, a position and an orientation of the camera relative to the event location. Based on the determined position and orientation of the camera, camera control system 300 may direct an automatic adjustment of the camera to capture the specific view of the event location.

In other examples in which the camera system is not physically coupled to a component of the surgical system, the spatial relationship between the camera and the event location may not be readily available or determinable from surgical session data alone. In such examples, to facilitate automatic adjustment of the view of the camera to capture the specific view of the event location, imagery captured by the camera of the camera system and 3D positional data tracked by the computer-assisted surgical system may be registered to a common 3D space. Additionally or alternatively, the camera system (e.g., camera 122 and/or camera manipulating system 124) may be registered to the common 3D space. As mentioned above, the computer-assisted surgical system may use kinematic information generated from surgical system sensors to track (e.g., determine positions of) various components of the surgical system within a 3D space. Registration of the imagery captured by the camera to the same 3D space used by the computer-assisted surgical system may allow camera control system 300 to use kinematic information associated with the computer-assisted surgical system, including the camera system, to determine a spatial relationship between the camera and the event location. Such spatial relationship information may be utilized by camera control system 300 to determine a direction and amount of adjustment of the position and/or orientation of the camera to capture a view of the event location. Even where tracking-based techniques are used to determine the component location (and hence the event location), registration may enable estimation of the position and/or orientation of the camera based on surgical session data and thereby speed up the tracker-based determination of the component location.

Camera control system 300 may be configured to perform the registration process once (e.g., as part of a calibration, setup procedure, or other initial registration) and/or periodically or continuously after initial registration to refine the initial registration (e.g., to account for changes in physical positions, which positions may have various kinematic errors) and/or to account for positional adjustments of surgical system components. Registration may be performed by any suitable registration technique, including but not limited to vision-based registration, model-based registration, and marker-based registration.

To illustrate, imagery captured by the camera may be used for the registration process. For example, camera control system 300 may determine, based on imagery captured by the camera and using a trained neural network, a location of a component included in the computer-assisted surgical system. In certain examples, this may include camera control system 300 using a trained neural network to identify an object of interest depicted in the imagery, associating the object of interest to a component of the surgical system in any suitable way (e.g., object recognition), and determining a location (e.g., an image-based location) of the object.

Camera control system 300 may then perform an optimization to fit a model of the surgical system component to the determined location of the object (e.g., to the location of the object in the images). For components that are positioned on a floor, such as carts 132, camera control system 300 may be configured to constrain the optimization to search only for solutions that are rotations and translations on the plane of the floor on which the components are placed. This constrained optimization may provide faster and/or more accurate results than a traditional optimization performed in all six degrees of freedom.

The registration process may be used by camera control system 300 to determine a missing link in a kinematic chain connecting the camera that is not physically coupled to a component of the computer-assisted surgical system. Camera control system 300 may represent the missing link as a transform that defines an estimated spatial relationship between the camera and the components of the surgical system. The transform may define a rotation and a translation that may be applied to convert data points from a reference frame of the camera to a reference frame of the computer-assisted surgical system (e.g., to convert coordinate points from a coordinate system of the camera to a coordinate system of the computer-assisted surgical system) and vice versa.

Camera control system 300 may use the missing link to complete a kinematic chain connecting a camera and the surgical system such that the complete kinematic chain is known and accessible to camera control system 300. Camera control system 300 may then use kinematics of the camera system to track the position of the camera and determine the appropriate positional and/or orientational adjustment of the camera to capture the view of the event location.

As mentioned, the imagery captured by the camera may be transmitted to and displayed by a display device associated with the computer-assisted surgical system and/or a display device associated with a remote computing device. In this way a surgical team member, a remote proctor, a remote technician, and the like may view contextual visual content associated with a surgical session event and use the contextual visual content, for example, to perform one or more tasks during the surgical session (e.g., to perform a surgical procedure, to monitor or train a surgical team member, to troubleshoot technical issues, etc.). Examples of this processing will now be described.

For example, if camera control system 300 detects that manipulator arm 118-1 is colliding with manipulator arm 118-2 (labeled "MA1_Collide_MA2" in table 900), camera control system 300 may determine that a location of the detected event is a location of manipulator arm 118-1 (labeled "MA1" in table 900). Based on this determination, camera control system 300 may utilize the surgical session data (e.g., kinematic data) to determine a location, within the surgical facility, of manipulator arm 118-1. Camera control system 300 may then direct camera manipulating system 124 to adjust a position and/or an orientation of camera 122 to capture a view of manipulator arm 118-1. The imagery captured by camera 122 may then be displayed on a display device associated with a surgical team member 114 (e.g., surgeon 114-1), thus allowing the surgical team member 114 to quickly identify why manipulator arm 118-1 is not moving.

As another example, if camera control system 300 determines that no signal is detected from a surgical instrument coupled to fourth manipulator arm 118-4 (labeled "MA4_NoSignal" in table 900), camera control system 300 may determine that a location of the detected event is a location on fourth manipulator arm 118-4 where the surgical instrument should be connected (labeled "MA4" in table 900). Based on this determination, camera control system 300 may utilize the surgical session data (e.g., kinematic data) to determine a location, within the surgical facility, of fourth manipulator arm 118-4. Camera control system 300 may then direct camera manipulating system 124 to adjust a position and/or an orientation of camera 122 to capture a view of fourth manipulator arm 118-4. The imagery captured by camera 122 may then be displayed on a display device associated with a surgical team member 114 (e.g., a user device used by assistant 114-3), thus allowing the surgical team member 114 to quickly determine if the surgical instrument is properly connected to fourth manipulator arm 118-4.

Figure 10:
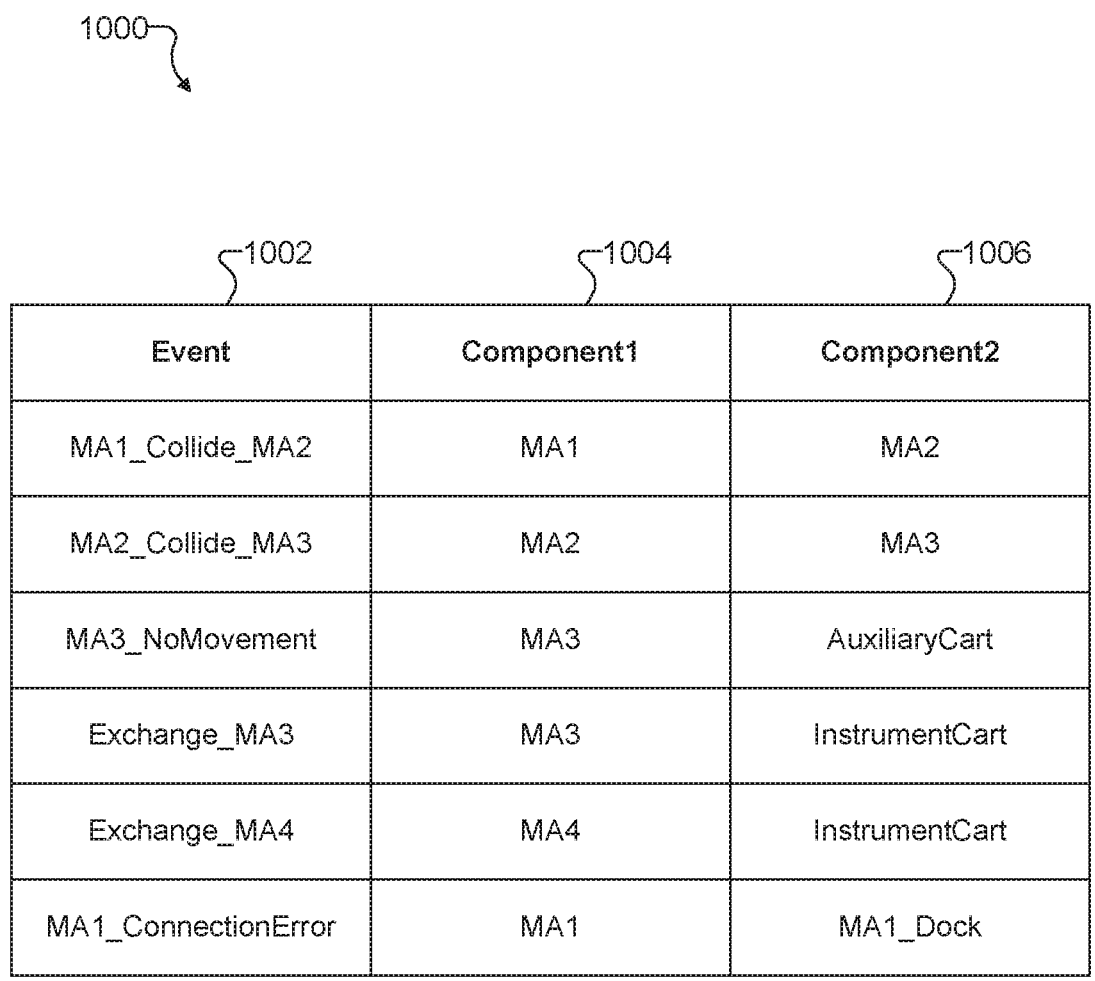

In some examples, a plurality of surgical system components may be associated with a particular event. For example, FIG. 10 shows an exemplary event location table 1000 that may be maintained or otherwise accessed by camera control system 300. As shown in column 1002, table 100 may include a plurality of entries representative of various events that may occur during a surgical session. As shown in column 1004, table 1000 may list a primary component associated with each event. As shown in column 1006, table 1000 may list a secondary component associated with each event. Camera control system 300 may determine the event location as the location of the primary component associated with the detected event. Camera control system 300 may then switch, in response to a location switch event, the event location to a location of the secondary component.

In some examples, the location switch event may include the passage of a predetermined period of time (e.g., 20 seconds) since a specific view of the primary component was first displayed. In some examples a user may specify the duration of the predetermined period of time.

Alternatively, the location switch event may be the receipt, by camera control system 300, of user input directing camera control system 300 to switch to the secondary location. The user input may be received by way of any suitable computing device associated with the computer-assisted surgical system (e.g., user device 502, remote computing system 402, or a computing device included in user control system 104, auxiliary system 106, or camera system 108).

To illustrate, if camera control system 300 detects that a surgical instrument coupled to manipulator arm 118-3 does not move when operated by surgeon 114-1 (labeled "MA3_NoMovement" in table 1000), camera control system 300 may determine that a primary location of the detected event is a location of manipulator arm 118-3 (labeled "MA3" in table 1000). Based on this determination, camera control system 300 may utilize the surgical session data (e.g., kinematic data) to determine a location, within the surgical facility, of manipulator arm 118-3. Camera control system 300 may then direct auxiliary camera system 108 to adjust a view of camera 122 to capture a specific view of manipulator arm 118-3. When the image captured by camera 122 is displayed on a display associated with user control system (e.g., on a touchscreen or on user device 502), a surgeon can quickly determine if the surgical instrument is not properly coupled to manipulator arm 118-3 or if manipulator arm 118-3 is colliding with another manipulator arm. The surgeon can then provide input via user control system 104 (e.g., via a touchpad or foot pedal on user control system 104) or user device 502 to view the secondary location. In response to this user input, camera control system 300 may direct auxiliary camera system 108 to adjust a view of camera 122 to capture a specific view of auxiliary cart 132-1. This may allow the surgeon to determine if a cable of the surgical instrument is properly connected to auxiliary cart 132-1.

In some examples, a user may be able to manually adjust the view of the camera after it has been adjusted to capture the view of the event location. Manual adjustments may include positional and/or orientational adjustments, as well as optical adjustments (e.g., zoom and focus adjustments).

In some examples, camera control system 300 may be configured to provide, for display by a display device associated with the computer-assisted surgical session, contextual information in addition to imagery captured by the camera. For example, camera control system 300 may identify contextual content associated with the identified surgical session event and/or the identified event location. The contextual content may be stored, for example, in table 900 or table 1000. The contextual content may include, for example, a message to be displayed with the imagery captured by the camera.

To illustrate, camera control system 300 may determine, based on surgical session data, user profile data, and/or user input data, that a surgical procedure has progressed to a stapling stage. As a result, camera control system 300 may direct an automatic adjustment of a camera to capture a specific view of a manipulator arm, and may direct a display device to display, along with the imagery of the manipulator arm, a message such as: "Replace this surgical instrument with a stapler instrument."

Additionally or alternatively, camera control system 300 may be configured to provide contextual information other than by way of a display device, such as by directing an illumination device (e.g., a task light, a laser light, etc.) to illuminate the event location. For instance, camera control system 300 may direct an adjustment of a laser device in the computer-assisted surgical session to illuminate the manipulator arm to which a surgical instrument should be coupled. Adjustment of the illumination device may be accomplished in a manner similar to the adjustment of the camera described herein.

Figure 11:
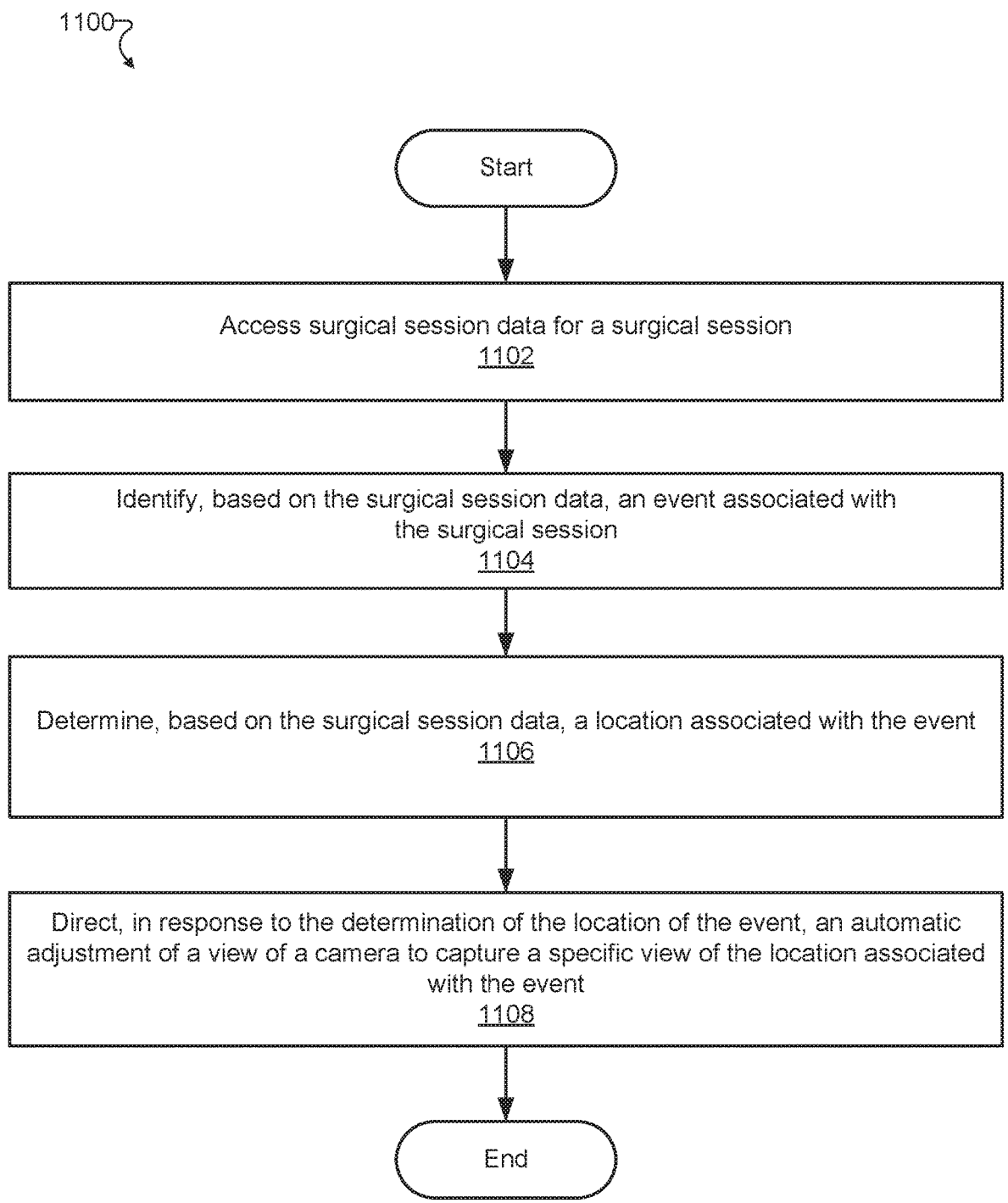
FIG. 11 illustrates an exemplary camera control method according to principles described herein.

FIG. 11 shows an exemplary camera control method 1100. While FIG. 11 illustrates exemplary operations according to one embodiment, other embodiments may omit, add to, reorder, combine, and/or modify any of the steps shown in FIG. 11. One or more of the operations shown in in FIG. 11 may be performed by camera control system 300, any components included therein, and/or any implementation thereof.

In step 1102, the camera control system accesses surgical session data for a surgical session. The surgical session includes performance of one or more operations by a computer-assisted surgical system. Step 1102 may be performed in any of the ways described herein.

In step 1104, the camera control system identifies, based on the surgical session data, an event associated with the surgical session. Step 1104 may be performed in any of the ways described herein.

In step 1106, the camera control system determines, based on the surgical session data, a location associated with the event. Step 1106 may be performed in any of the ways described herein.

In step 1108, the camera control system directs, in response to the determination of the location of the event, an automatic adjustment of a view of a camera to capture a specific view of the location associated with the event. Step 1108 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 12:
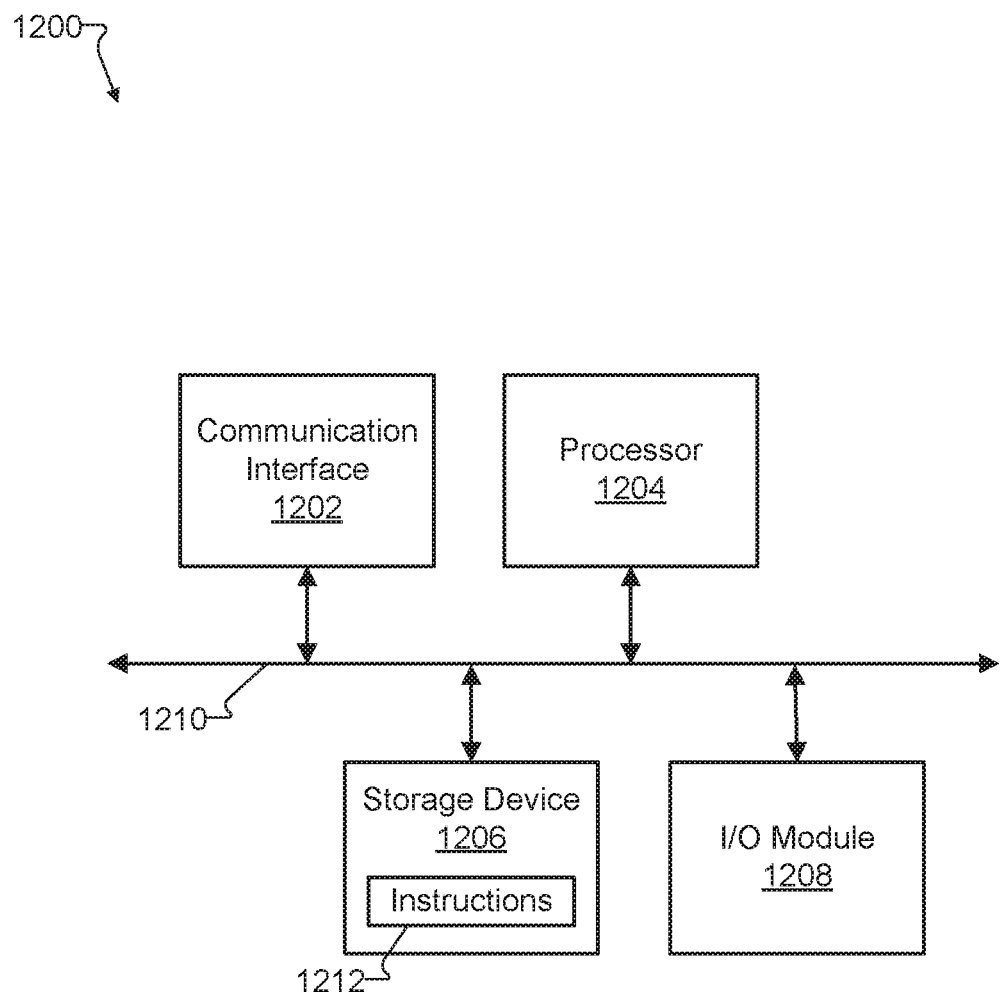
FIG. 12 illustrates an exemplary computing system according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, VO module 1208 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1200. For example, processing facility 304 may be implemented by processor 1204 and storage facility 302 may be implemented by storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
 access, during a surgical session performed with a computer-assisted surgical system, surgical session data generated by the computer-assisted surgical system during the surgical session, the surgical session including performance of one or more operations by the computer-assisted surgical system;
 identify, based on the surgical session data, an event associated with the surgical session;
 determine a location associated with the event; and
 direct, in response to the determination of the location of the event, an automatic adjustment of a view of a camera to capture a view of the location associated with the event.

2. The system of claim 1, wherein the determination of the location associated with the event comprises:
identifying, in response to the identification of the event, a component, of the computer-assisted surgical system, that is associated with the event; and
determining a location of the component associated with the event.

3. The system of claim 2, wherein the determining of the location of the component associated with the event is based on kinematic data representative of a position of the component associated with the event.

4. The system of claim 2, wherein the determining of the location of the component associated with the event is based on at least one of a marker provided on the component associated with the event and a signal emitted from the component associated with the event.

5. The system of claim 1, wherein the directing of the automatic adjustment of the view of the camera comprises directing an adjustment of at least one of an orientation of the camera and a position of the camera to capture the view of the location associated with the event.

6. The system of claim 1, wherein the processor is further configured to execute the instructions to register imagery of the camera and three-dimensional ("3D") positional data tracked by the computer-assisted surgical system to a common 3D space.

7. The system of claim 1, wherein the camera is coupled to a component 7. of the computer-assisted surgical system.

8. The system of claim 1, wherein the surgical session data comprises data representative of the one or more operations performed by the computer-assisted surgical system during the surgical session.

9. The system of claim 1, wherein the surgical session data comprises kinematic data representative of at least one of a position, a pose, and an orientation of a component of the computer-assisted surgical system.

10. The system of claim 1, wherein the surgical session data comprises image data representative of one or more images captured by at least one of the camera and an imaging device coupled to a manipulator arm of the computer-assisted surgical system.

11. The system of claim 1, wherein the surgical session data comprises data generated based on user input received during the surgical session by way of a user device communicatively paired with the computer-assisted surgical system during the surgical session.

12. The system of claim 11, wherein the user input specifies a task performed by the computer-assisted surgical system or a surgical team member during the surgical session.

13. The system of claim 1, wherein the processor is further configured to execute the instructions to:
   access at least one of
      historical surgical session data generated during one or more additional surgical sessions that precede the surgical session, and
      global surgical session data generated based on operations performed by one or more computer-assisted surgical systems other than the computer-assisted surgical system; and
   apply at least one of the historical surgical session data and the global surgical session data to a machine learning model executed by at least one physical computing device;
   wherein the machine learning model uses the at least one of the historical surgical session data and the global surgical session data to associate patterns of surgical system operations with a plurality of events.

14. A method comprising:
   accessing, by a camera control system during a surgical session performed with a computer-assisted surgical system, surgical session data generated by the computer-assisted surgical system during the surgical session, the surgical session including performance of one or more operations by a computer-assisted surgical system;
   identifying, by the camera control system based on the surgical session data, an event associated with the surgical session;
   determining, by the camera control system, a location associated with the event; and
   directing, by the camera control system in response to the determination of the location of the event, an automatic adjustment of a view of a camera to capture a view of the location associated with the event.

15. The method of claim 14, wherein the determining of the location associated with the event comprises:
   identifying, in response to the identification of the event, a component, of the computer-assisted surgical system, that is associated with the event; and
   determining a location of the component associated with the event.

16. The method of claim 15, wherein the determining of the location of the component associated with the event is based on kinematic data representative of a position of the component associated with the event.

17. The method of claim 15, wherein the determining of the location of the component associated with the event is based on at least one of a marker provided on the component associated with the event and a signal emitted from the component associated with the event.

18. The method of claim 14, wherein the directing of the automatic adjustment of the view of the camera comprises directing an adjustment of at least one of an orientation of the camera and a position of the camera to capture the view of the location associated with the event.

19. The method of claim 14, further comprising:
   registering, by the camera control system, imagery of the camera and three-dimensional ("3D") positional data tracked by the computer-assisted surgical system to a common 3D space.

20. A system, comprising:
   a memory storing instructions; and
   a processor communicatively coupled to the memory and configured to execute the instructions to:
      receive, from a user device communicatively paired with a computer-assisted surgical system during a surgical session performed with the computer-assisted surgical system, user input indicating a workflow segmentation of the surgical session;
      identify, based at least in part on the user input, an event associated with the surgical session;
      determine a location associated with the identified event; and
      direct, in response to the determination of the location of the event, an automatic adjustment of a view of a camera to capture a view of the location associated with the event.

* * * * *

UNITED STATES PATENT AND TRADEMARK OFFICE
CERTIFICATE OF CORRECTION

PATENT NO. : 12,220,181 B2  
APPLICATION NO. : 17/426038  
DATED : February 11, 2025  
INVENTOR(S) : Govinda Payyavula et al.

Page 1 of 1

It is certified that error appears in the above-identified patent and that said Letters Patent is hereby corrected as shown below:

In the Claims

Column 22, Claim 7, Line 57, "7." should be deleted.

Signed and Sealed this  
Eighteenth Day of March, 2025

Coke Morgan Stewart  
*Acting Director of the United States Patent and Trademark Office*